United States Patent [19]
Skatrud et al.

[11] Patent Number: 5,945,324
[45] Date of Patent: Aug. 31, 1999

[54] **MULTIPLE DRUG RESISTANCE GENE ATRC OF *ASPERGILLUS NIDULANS***

[75] Inventors: Paul Luther Skatrud, Greenwood, Ind.; Maarten A. de Waard; Alan C. Andrade, both of Wageningen, Netherlands; Robert Brown Peery, Brownsburg, Ind.

[73] Assignee: Eli Lilly and Company, Indianapolis, Ind.

[21] Appl. No.: 08/996,644

[22] Filed: Dec. 23, 1997

[51] Int. Cl.[6] .............................. C12N 9/16; C12N 15/00; C12N 1/20; C07H 21/04
[52] U.S. Cl. ................. 435/196; 435/252.3; 435/254.11; 435/320.1; 435/325; 435/410; 435/455; 435/468; 435/471; 536/23.2
[58] Field of Search ................................. 435/196, 252.3, 435/254.11, 320.1, 325, 410, 455, 468, 471; 536/23.2

[56] References Cited

U.S. PATENT DOCUMENTS

| | | | |
|---|---|---|---|
| 5,516,655 | 5/1996 | Peery et al. | 435/69.1 |
| 5,705,352 | 1/1998 | Peery et al. | 435/7.31 |
| 5,773,214 | 6/1998 | Peery et al. | 435/6 |
| 5,786,463 | 7/1998 | Peery et al. | 536/23.1 |

OTHER PUBLICATIONS

G. Del Sorbo, et al. "Multidrug resistance in *Aspergillus nidulans* involves novel ATP–binding cassette transporters." *Mol. Gen. Genet.* 254:417–426 (1997).

M. B. Tobin, et al. "Genes encoding multiple drug resistance–like proteins in *Aspergillus fumigatus* and *Aspergillus flavus*." Gene 200:11–23 (1997).

S. J. Thornewell, et al. "Cloning and characterization of CneMDRl: a *Cryptococcus neoformans* gene encoding a protein related to multidrug resistance proteins." *Gene* 201:21–29 (1997).

*Primary Examiner*—Robert A. Wax
*Assistant Examiner*—Einar Stole
*Attorney, Agent, or Firm*—Thomas D. Webster

[57] ABSTRACT

The invention provides isolated nucleic acid compounds encoding a multiple drug resistance protein of *Aspergillus nidulans*. Vectors and transformed host cells comprising the multiple drug resistance-encoding DNA of *Aspergillus nidulans* atrC are also provided. The invention further provides assays which utilize these transformed host cells.

9 Claims, No Drawings

15,945,324

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 3927 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..3924

(xi) SEQUENCE DESCRIPTION: SEQ ID NO:1:

```
ATG CGG AGG CTC GGA CCC TCA GTT TAC CGG CGT TCG GAC GTG TCT ACT        48
Met Arg Arg Leu Gly Pro Ser Val Tyr Arg Arg Ser Asp Val Ser Thr
 1               5                  10                  15

TTA AAA AAA AAG AAG CTC TCG TTG TCA CCA TCG TCA TGC TCG ACC GCG        96
Leu Lys Lys Lys Lys Leu Ser Leu Ser Pro Ser Ser Cys Ser Thr Ala
            20                  25                  30

GCT GTA CCA GAC TCC GTC TCA GGA CGA GTC GAC CAC CAG TGT ACC ATG       144
Ala Val Pro Asp Ser Val Ser Gly Arg Val Asp His Gln Cys Thr Met
        35                  40                  45

CAC GGA GGC GCC TCT GGT CGA GGA AGG GGA GGA AGC AAG CTT TGG CGC       192
His Gly Gly Ala Ser Gly Arg Gly Arg Gly Gly Ser Lys Leu Trp Arg
 50                  55                  60

ATA CAA GGT GCC AAG CTG ATA TGC TCG CGC AAA AGA GGA TCT TTA CAT       240
Ile Gln Gly Ala Lys Leu Ile Cys Ser Arg Lys Arg Gly Ser Leu His
 65                  70                  75                  80

TCG CCG GCA GGA CAG AAC TTA TCC TTC AGG CCG TTG CTA TCC TTG CTG       288
Ser Pro Ala Gly Gln Asn Leu Ser Phe Arg Pro Leu Leu Ser Leu Leu
                85                  90                  95

CAT GCG CCT CTG GAG CAG GAA TTG CGC TTC AAA ACC TCA TCT TCG GCC       336
His Ala Pro Leu Glu Gln Glu Leu Arg Phe Lys Thr Ser Ser Ser Ala
           100                 105                 110

AGT TCG TCA CCG TCA TCA CCG ATT TCA CCA ACG GAA TCT CAA CGC CGG       384
Ser Ser Ser Pro Ser Ser Pro Ile Ser Pro Thr Glu Ser Gln Arg Arg
       115                 120                 125

CAG ACT TTC GTG ACA ATG CCG CCG AGT TGG CGT ATC CTC TAC TTT GTA       432
Gln Thr Phe Val Thr Met Pro Pro Ser Trp Arg Ile Leu Tyr Phe Val
   130                 135                 140

TAC CTG GGC ATC GCG CGG CTC GTC CTC TCC TAC ACC TAC AAC ACC CTC       480
Tyr Leu Gly Ile Ala Arg Leu Val Leu Ser Tyr Thr Tyr Asn Thr Leu
145                 150                 155                 160

CTA ACC TAC GCG GCC TAC CGC ATC GTC CGC AAT ATC CGA CAC GCC TAT       528
Leu Thr Tyr Ala Ala Tyr Arg Ile Val Arg Asn Ile Arg His Ala Tyr
                165                 170                 175

CTC AAA GCG GCG CTG AGC CAA GAA GTG GCA TAC TAC GAT TTC GGT AGC       576
Leu Lys Ala Ala Leu Ser Gln Glu Val Ala Tyr Tyr Asp Phe Gly Ser
           180                 185                 190

GGG GGC TCC ATC GCC GCG CAG GCA ACT TCG AAC GGC AAA CTG ATC CAG       624
Gly Gly Ser Ile Ala Ala Gln Ala Thr Ser Asn Gly Lys Leu Ile Gln
       195                 200                 205

GCC GGC GCC TCG GAT AAG ATC GGT CTT CTC TTC CAG GGC CTC GCA GCA       672
Ala Gly Ala Ser Asp Lys Ile Gly Leu Leu Phe Gln Gly Leu Ala Ala
   210                 215                 220

TTC GTG ACG CTT TCA TTA TCG CGT TTG TGG TGC AAG TGG AAA CTC ACT       720
Phe Val Thr Leu Ser Leu Ser Arg Leu Trp Cys Lys Trp Lys Leu Thr
225                 230                 235                 240

CTG ATC TGC ATC TGC ATC CCC GTA GCC ACG ATC GGC ACG ACG GGG GTG       768
Leu Ile Cys Ile Cys Ile Pro Val Ala Thr Ile Gly Thr Thr Gly Val
                245                 250                 255

GTA GCT GCG GTC GAG GCT GGG CAC GAG ACG AGG ATC TTG CAG ATA CAT       816
Val Ala Ala Val Glu Ala Gly His Glu Thr Arg Ile Leu Gln Ile His
           260                 265                 270

GCG CAG GCG AAT TCG TTT GCC GAG GGT ATT CTG GCG GGT GTG AAG GCT       864
Ala Gln Ala Asn Ser Phe Ala Glu Gly Ile Leu Ala Gly Val Lys Ala
```

-continued

```
              275                 280                 285
GTT CAT GCT TTT GGG ATG CGG GAT AGT CTG GTC AGG AAG TTT GAT GAA       912
Val His Ala Phe Gly Met Arg Asp Ser Leu Val Arg Lys Phe Asp Glu
    290                 295                 300

TAT CTG GTG GAG GCG CAT AAG GTC GGT AAG AAG ATC TCG CCG CTG CTT       960
Tyr Leu Val Glu Ala His Lys Val Gly Lys Lys Ile Ser Pro Leu Leu
305                 310                 315                 320

GGT CTT CTC TTC TCG GCG GAG TAT ACG ATC ATC TAC CTT GGA TAT GGG      1008
Gly Leu Leu Phe Ser Ala Glu Tyr Thr Ile Ile Tyr Leu Gly Tyr Gly
                325                 330                 335

CTG GCG TTT TGG CAG GGG ATC CAT ATG TTC GGC AGG GGG GAG ATT GGG      1056
Leu Ala Phe Trp Gln Gly Ile His Met Phe Gly Arg Gly Glu Ile Gly
            340                 345                 350

ACT GCT GGG GAT ATC TTT ACG GTT TTG CTC TCT GTC GTC ATT GCG TCA      1104
Thr Ala Gly Asp Ile Phe Thr Val Leu Leu Ser Val Val Ile Ala Ser
                355                 360                 365

ATC AAC CTG ACT TTA CTG GCG CCG TAT TCA ATT GAA TTT AGC AGG GCT      1152
Ile Asn Leu Thr Leu Leu Ala Pro Tyr Ser Ile Glu Phe Ser Arg Ala
    370                 375                 380

GCT TCA GCG GCT GCG CAA CTG TTC CGA CTC ATA GAT CGA GAG TCT GAA      1200
Ala Ser Ala Ala Ala Gln Leu Phe Arg Leu Ile Asp Arg Glu Ser Glu
385                 390                 395                 400

ATC AAC CCA TAC GGG AAG GAA GGC CTC GAG CCG GAA CGG GTA TTA GGC      1248
Ile Asn Pro Tyr Gly Lys Glu Gly Leu Glu Pro Glu Arg Val Leu Gly
                405                 410                 415

GAC GTC GAG CTC GAG AAT GTT ACG TTC TCG TAT CCC ACG AGG CCG GGG      1296
Asp Val Glu Leu Glu Asn Val Thr Phe Ser Tyr Pro Thr Arg Pro Gly
            420                 425                 430

ATT ACC GTC CTC GAT AAC TTC AGT CTC AAG GTC CCA GCG GGA AAG GTG      1344
Ile Thr Val Leu Asp Asn Phe Ser Leu Lys Val Pro Ala Gly Lys Val
                435                 440                 445

ACT GCC CTG GTA GGG CAA TCT GGA TCG GGG AAG AGC ACG ATC GTG GGA      1392
Thr Ala Leu Val Gly Gln Ser Gly Ser Gly Lys Ser Thr Ile Val Gly
    450                 455                 460

TTG CTC GAG CGG TGG TAT AAC CCG ACC TCT GGG GCG ATC AGA CTC GAC      1440
Leu Leu Glu Arg Trp Tyr Asn Pro Thr Ser Gly Ala Ile Arg Leu Asp
465                 470                 475                 480

GGG AAC CTG ATC AGT GAG CTC AAT GTT GGC TGG CTG CGG AGG AAT GTG      1488
Gly Asn Leu Ile Ser Glu Leu Asn Val Gly Trp Leu Arg Arg Asn Val
                485                 490                 495

CGG CTC GTA CAG CAG GAG CCG GTG CTC TTC CAG GGA AGC GTG TTC GAT      1536
Arg Leu Val Gln Gln Glu Pro Val Leu Phe Gln Gly Ser Val Phe Asp
            500                 505                 510

AAC ATC AGG TAC GGC CTC GTC GGG ACG CCG TGG GAG AAT GCC TCT CGG      1584
Asn Ile Arg Tyr Gly Leu Val Gly Thr Pro Trp Glu Asn Ala Ser Arg
    515                 520                 525

GAA GAG CAG ATG GAA CGG GTG CAG GAG GCC GCG AAG TTG GCA TAT GCG      1632
Glu Glu Gln Met Glu Arg Val Gln Glu Ala Ala Lys Leu Ala Tyr Ala
530                 535                 540

CAC GAA TTC ATC TCT GAG CTG ACC GAC GGA TAC GAT ACG CTG ATC GGC      1680
His Glu Phe Ile Ser Glu Leu Thr Asp Gly Tyr Asp Thr Leu Ile Gly
545                 550                 555                 560

GAA CGG GGT GGT CTG CTT TCT GGA GGC CAG AAG CAG CGG GTT GCG ATT      1728
Glu Arg Gly Gly Leu Leu Ser Gly Gly Gln Lys Gln Arg Val Ala Ile
                565                 570                 575

GCC CGC AGC GTC GTT TCT CAA CCG AAG GTC CTT CTG CTG GAT GAA GCA      1776
Ala Arg Ser Val Val Ser Gln Pro Lys Val Leu Leu Leu Asp Glu Ala
            580                 585                 590

ACC AGT GCT CTT GAT CCG CAT GCA GAG ACG ATT GTT CAG AAG GCT CTG      1824
Thr Ser Ala Leu Asp Pro His Ala Glu Thr Ile Val Gln Lys Ala Leu
```

-continued

```
              595                    600                      605
GAC AAA GCA GCT GAG GGG CGC ACG ACG ATT GTC ATT GCT CAC AAA CTT      1872
Asp Lys Ala Ala Glu Gly Arg Thr Thr Ile Val Ile Ala His Lys Leu
    610                 615                      620

GCT ACG ATC CGC AAG GCG GAC AAT ATC GTT GTC ATG AGC AAG GGT CAC      1920
Ala Thr Ile Arg Lys Ala Asp Asn Ile Val Val Met Ser Lys Gly His
625                 630                  635                 640

ATT GTC GAG CAA GGC ACA CAC GAG TCA CTG ATA GCC AAG GAC GGC GTC      1968
Ile Val Glu Gln Gly Thr His Glu Ser Leu Ile Ala Lys Asp Gly Val
                645                 650                 655

TAT GCC GGT CTG GTC AAA ATC CAG AAC CTG GCA GTG AAT GCT TCA GCA      2016
Tyr Ala Gly Leu Val Lys Ile Gln Asn Leu Ala Val Asn Ala Ser Ala
            660                 665                 670

CAT GAC AAT GTA AAT GAG GAG GGT GAA GGC GAA GAT GTC GCT CTC CTG      2064
His Asp Asn Val Asn Glu Glu Gly Glu Gly Glu Asp Val Ala Leu Leu
            675                 680                 685

GAG GTC ACC GAA ACA GCA GTA ACC CGC TAC CCA ACC TCC ATC CGC GGT      2112
Glu Val Thr Glu Thr Ala Val Thr Arg Tyr Pro Thr Ser Ile Arg Gly
        690                 695                 700

CGA ATG AAC TCC ATA AAG GAC CGC GAC GAT TAT GAG AAC CAC AAG CAC      2160
Arg Met Asn Ser Ile Lys Asp Arg Asp Asp Tyr Glu Asn His Lys His
705                 710                 715                 720

ATG GAT ATG CTG GCC GCC TTA GCT TAT CTC GTC CGC GAA TGT CCA GAA      2208
Met Asp Met Leu Ala Ala Leu Ala Tyr Leu Val Arg Glu Cys Pro Glu
                725                 730                 735

CTG AAA TGG GCC TAT CTC GTC GTG CTA CTG GGG TGT CTT GGT GGT TGC      2256
Leu Lys Trp Ala Tyr Leu Val Val Leu Leu Gly Cys Leu Gly Gly Cys
            740                 745                 750

GCC ATG TAC CCC GGC CAA GCT ATC TTG ATG TCT CGC GTT GTC GAG GTC      2304
Ala Met Tyr Pro Gly Gln Ala Ile Leu Met Ser Arg Val Val Glu Val
            755                 760                 765

TTC ACG CTC TCG GGA GAC GCT ATG CTA GAC AAA GGA GAC TTC TAT GCC      2352
Phe Thr Leu Ser Gly Asp Ala Met Leu Asp Lys Gly Asp Phe Tyr Ala
        770                 775                 780

AGT ATG CTG ATC GTT CTC GCG GCC GGG TGT CTG ATC TGT TAC TTA GCT      2400
Ser Met Leu Ile Val Leu Ala Ala Gly Cys Leu Ile Cys Tyr Leu Ala
785                 790                 795                 800

GTC GGA TAT GCA ACC AAC ACT ATA GCC CAG CAT CTT AGT CAT TGG TTT      2448
Val Gly Tyr Ala Thr Asn Thr Ile Ala Gln His Leu Ser His Trp Phe
                805                 810                 815

CGA CGC CTC ATT CTG CAC GAC ATG CTG CGA CAG GAT ATC CAG TTC TTT      2496
Arg Arg Leu Ile Leu His Asp Met Leu Arg Gln Asp Ile Gln Phe Phe
            820                 825                 830

GAC CGT GAA GAG AAC ACT ACC GGT GCG CTG GTA AGC CGT ATC GAT TCG      2544
Asp Arg Glu Glu Asn Thr Thr Gly Ala Leu Val Ser Arg Ile Asp Ser
        835                 840                 845

TAC CCG CAT GCA ATT CTC GAA CTG ATG GGC TAC AAC ATC GCC CTG GTC      2592
Tyr Pro His Ala Ile Leu Glu Leu Met Gly Tyr Asn Ile Ala Leu Val
850                 855                 860

GTG ATT GCT GTC CTG CAG GTG GTA ACC TGT GGC ATC CTG GCC ATT GCA      2640
Val Ile Ala Val Leu Gln Val Val Thr Cys Gly Ile Leu Ala Ile Ala
865                 870                 875                 880

TTC TCC TGG AAA CTA GGG CTG GTC GTT GTC TTT GGC GGT ATT CCA CCC      2688
Phe Ser Trp Lys Leu Gly Leu Val Val Val Phe Gly Gly Ile Pro Pro
                885                 890                 895

CTT GTC GGT GCT GGG ATG GTA CGA ATC CGC GTC GAC TCC CGC CTC GAT      2736
Leu Val Gly Ala Gly Met Val Arg Ile Arg Val Asp Ser Arg Leu Asp
            900                 905                 910

CGC CAG ACA TCG AAG AAA TAT GGC ACC AGC TCG TCC ATT GCC TCT GAA      2784
Arg Gln Thr Ser Lys Lys Tyr Gly Thr Ser Ser Ser Ile Ala Ser Glu
```

```
                915                 920                 925
GCT GTA AAC GCT ATC CGG ACC GTT TCG TCC CTT GCA ATC GAA GAG ACG    2832
Ala Val Asn Ala Ile Arg Thr Val Ser Ser Leu Ala Ile Glu Glu Thr
        930                 935                 940

GTG CTA CGT CGA TAC ACG GAG GAA CTA GAC CAC GCT GTC TCG TCT TCG    2880
Val Leu Arg Arg Tyr Thr Glu Glu Leu Asp His Ala Val Ser Ser Ser
945                 950                 955                 960

GTG AAA CCC ATG GCT GCC ACG ATG ATT TGT TTC GGG CTG ACG CAG TGC    2928
Val Lys Pro Met Ala Ala Thr Met Ile Cys Phe Gly Leu Thr Gln Cys
            965                 970                 975

ATT GAG TAC TGG TTT CAG GCG CTG GGA TTC TGG TAT GGG TGT CGT CTT    2976
Ile Glu Tyr Trp Phe Gln Ala Leu Gly Phe Trp Tyr Gly Cys Arg Leu
                980                 985                 990

GTG TCG CTG GGG GAG ACT AGC ATG TAT AGT TTC TTT GTC GCA TTC CTC    3024
Val Ser Leu Gly Glu Thr Ser Met Tyr Ser Phe Phe Val Ala Phe Leu
                    995                 1000                1005

AGT GTG TTC TTT GCG GGT CAG GCG TCA GCG CAG CTG TTC CAG TGG TCG    3072
Ser Val Phe Phe Ala Gly Gln Ala Ser Ala Gln Leu Phe Gln Trp Ser
1010                1015                1020

ACC AGT ATT ACA AAG GGA ATC AAT GCG ACG AAC TAC ATC GCT TGG TTG    3120
Thr Ser Ile Thr Lys Gly Ile Asn Ala Thr Asn Tyr Ile Ala Trp Leu
1025                1030                1035                1040

CAC CAG CTC CAA CCA ACA GTG CGC GAG ACG CCG GAG AAC CAC GAT AAA    3168
His Gln Leu Gln Pro Thr Val Arg Glu Thr Pro Glu Asn His Asp Lys
                    1045                1050                1055

GGC CCT GGA TCT GGG GCG CCG ATT GCT ATG GAC AAT GTG CGC TTC TCG    3216
Gly Pro Gly Ser Gly Ala Pro Ile Ala Met Asp Asn Val Arg Phe Ser
                    1060                1065                1070

TAC CCT CTA CGG CCA GAC GCC CCT ATC CTG AAA GGG GTG AAT CTG AAG    3264
Tyr Pro Leu Arg Pro Asp Ala Pro Ile Leu Lys Gly Val Asn Leu Lys
            1075                1080                1085

ATA AAC AAA GGC CAA TTC ATC GCT TTC GTC GGC TCC TCC GGC TGC GGC    3312
Ile Asn Lys Gly Gln Phe Ile Ala Phe Val Gly Ser Ser Gly Cys Gly
        1090                1095                1100

AAA TCC ACC ATG ATT GCC ATG CTC GAG CGC TTC TAC GAT CCA ACA ACA    3360
Lys Ser Thr Met Ile Ala Met Leu Glu Arg Phe Tyr Asp Pro Thr Thr
1105                1110                1115                1120

GGG AGC ATC ACA ATC GAC GCT TCC ACC CTC ACC GAC ATA AAC CCC ATA    3408
Gly Ser Ile Thr Ile Asp Ala Ser Thr Leu Thr Asp Ile Asn Pro Ile
                    1125                1130                1135

TCC TAC CGA AAT ATT GTG GCA CTG GTG CAG CAA GAG CCA ACC CTT TTC    3456
Ser Tyr Arg Asn Ile Val Ala Leu Val Gln Gln Glu Pro Thr Leu Phe
                    1140                1145                1150

CAA GGG ACA ATA CGG GAC AAC ATC TCG CTT GGC GAT GCA GTG AAG TCC    3504
Gln Gly Thr Ile Arg Asp Asn Ile Ser Leu Gly Asp Ala Val Lys Ser
            1155                1160                1165

GTG TCT GAT GAG CAG ATT GAG TCG GCC CTC CGC GCA GCT AAT GCC TGG    3552
Val Ser Asp Glu Gln Ile Glu Ser Ala Leu Arg Ala Ala Asn Ala Trp
1170                1175                1180

GAC TTT GTC TCC TCA TTG CCG CAG GGG ATC TAC ACG CCC GCT GGC TCA    3600
Asp Phe Val Ser Ser Leu Pro Gln Gly Ile Tyr Thr Pro Ala Gly Ser
1185                1190                1195                1200

GGC GGG TCC CAA CTC TCT GGG GGG CAG CGG CAA CGC ATT GCC ATT GCC    3648
Gly Gly Ser Gln Leu Ser Gly Gly Gln Arg Gln Arg Ile Ala Ile Ala
                    1205                1210                1215

CGC GCG CTC ATC CGA GAT CCA AAG ATC TTA CTC CTT GAC GAG GCT ACG    3696
Arg Ala Leu Ile Arg Asp Pro Lys Ile Leu Leu Leu Asp Glu Ala Thr
                    1220                1225                1230

AGT GCC CTG GAT ACA GAG AGT GAG AAG ATC GTG CAG AAG GCT CTC GAG    3744
Ser Ala Leu Asp Thr Glu Ser Glu Lys Ile Val Gln Lys Ala Leu Glu
```

-continued

```
                   1235                1240                1245
GGG GCG GCC AGG GAC GGG GAC CGG CTT ACG GTT GCT GTT GCG CAT CGA        3792
Gly Ala Ala Arg Asp Gly Asp Arg Leu Thr Val Ala Val Ala His Arg
        1250                1255                1260

TTA AGC ACG ATT AAG GAT GCT AAT GTT ATC TGT GTA TTC TTT GGA GGA        3840
Leu Ser Thr Ile Lys Asp Ala Asn Val Ile Cys Val Phe Phe Gly Gly
1265                1270                1275                1280

AAG ATT GCG GAG ATG GGA ACG CAT CAA GAG TTA ATA GTT AGG GGG GGG        3888
Lys Ile Ala Glu Met Gly Thr His Gln Glu Leu Ile Val Arg Gly Gly
            1285                1290                1295

CTG TAT AGA CGG ATG TGT GAG GCG CAG GCC TTG GAC TAA                    3927
Leu Tyr Arg Arg Met Cys Glu Ala Gln Ala Leu Asp
        1300                1305
```

(2) INFORMATION FOR SEQ ID NO:2:

(i) SEQUENCE CHARACTERISTICS:
        (A) LENGTH: 1308 amino acids
        (B) TYPE: amino acid
        (D) TOPOLOGY: linear (ii) MOLECULE TYPE: protein (xi) SEQUENCE DESCRIPTION: SEQ ID NO:2:

```
Met Arg Arg Leu Gly Pro Ser Val Tyr Arg Arg Ser Asp Val Ser Thr
1               5                   10                  15

Leu Lys Lys Lys Lys Leu Ser Leu Ser Pro Ser Ser Cys Ser Thr Ala
            20                  25                  30

Ala Val Pro Asp Ser Val Ser Gly Arg Val Asp His Gln Cys Thr Met
        35                  40                  45

His Gly Gly Ala Ser Gly Arg Gly Arg Gly Ser Lys Leu Trp Arg
    50                  55                  60

Ile Gln Gly Ala Lys Leu Ile Cys Ser Arg Lys Arg Gly Ser Leu His
65                  70                  75                  80

Ser Pro Ala Gly Gln Asn Leu Ser Phe Arg Pro Leu Leu Ser Leu Leu
                85                  90                  95

His Ala Pro Leu Glu Gln Glu Leu Arg Phe Lys Thr Ser Ser Ser Ala
            100                 105                 110

Ser Ser Ser Pro Ser Ser Pro Ile Ser Pro Thr Glu Ser Gln Arg Arg
        115                 120                 125

Gln Thr Phe Val Thr Met Pro Pro Ser Trp Arg Ile Leu Tyr Phe Val
    130                 135                 140

Tyr Leu Gly Ile Ala Arg Leu Val Leu Ser Tyr Thr Tyr Asn Thr Leu
145                 150                 155                 160

Leu Thr Tyr Ala Ala Tyr Arg Ile Val Arg Asn Ile Arg His Ala Tyr
                165                 170                 175

Leu Lys Ala Ala Leu Ser Gln Glu Val Ala Tyr Tyr Asp Phe Gly Ser
            180                 185                 190

Gly Gly Ser Ile Ala Ala Gln Ala Thr Ser Asn Gly Lys Leu Ile Gln
        195                 200                 205

Ala Gly Ala Ser Asp Lys Ile Gly Leu Leu Phe Gln Gly Leu Ala Ala
    210                 215                 220

Phe Val Thr Leu Ser Leu Ser Arg Leu Trp Cys Lys Trp Lys Leu Thr
225                 230                 235                 240

Leu Ile Cys Ile Cys Ile Pro Val Ala Thr Ile Gly Thr Thr Gly Val
                245                 250                 255

Val Ala Ala Val Glu Ala Gly His Glu Thr Arg Ile Leu Gln Ile His
            260                 265                 270
```

-continued

```
Ala Gln Ala Asn Ser Phe Ala Glu Gly Ile Leu Ala Gly Val Lys Ala
        275                 280                 285

Val His Ala Phe Gly Met Arg Asp Ser Leu Val Arg Lys Phe Asp Glu
        290                 295                 300

Tyr Leu Val Glu Ala His Lys Val Gly Lys Lys Ile Ser Pro Leu Leu
305                 310                 315                 320

Gly Leu Leu Phe Ser Ala Glu Tyr Thr Ile Ile Tyr Leu Gly Tyr Gly
                325                 330                 335

Leu Ala Phe Trp Gln Gly Ile His Met Phe Gly Arg Gly Glu Ile Gly
                340                 345                 350

Thr Ala Gly Asp Ile Phe Thr Val Leu Leu Ser Val Val Ile Ala Ser
            355                 360                 365

Ile Asn Leu Thr Leu Leu Ala Pro Tyr Ser Ile Glu Phe Ser Arg Ala
        370                 375                 380

Ala Ser Ala Ala Ala Gln Leu Phe Arg Leu Ile Asp Arg Glu Ser Glu
385                 390                 395                 400

Ile Asn Pro Tyr Gly Lys Glu Gly Leu Glu Pro Glu Arg Val Leu Gly
                405                 410                 415

Asp Val Glu Leu Glu Asn Val Thr Phe Ser Tyr Pro Thr Arg Pro Gly
                420                 425                 430

Ile Thr Val Leu Asp Asn Phe Ser Leu Lys Val Pro Ala Gly Lys Val
            435                 440                 445

Thr Ala Leu Val Gly Gln Ser Gly Ser Gly Lys Ser Thr Ile Val Gly
        450                 455                 460

Leu Leu Glu Arg Trp Tyr Asn Pro Thr Ser Gly Ala Ile Arg Leu Asp
465                 470                 475                 480

Gly Asn Leu Ile Ser Glu Leu Asn Val Gly Trp Leu Arg Arg Asn Val
                485                 490                 495

Arg Leu Val Gln Gln Glu Pro Val Leu Phe Gln Gly Ser Val Phe Asp
                500                 505                 510

Asn Ile Arg Tyr Gly Leu Val Gly Thr Pro Trp Glu Asn Ala Ser Arg
            515                 520                 525

Glu Glu Gln Met Glu Arg Val Gln Glu Ala Ala Lys Leu Ala Tyr Ala
        530                 535                 540

His Glu Phe Ile Ser Glu Leu Thr Asp Gly Tyr Asp Thr Leu Ile Gly
545                 550                 555                 560

Glu Arg Gly Gly Leu Leu Ser Gly Gly Gln Lys Gln Arg Val Ala Ile
                565                 570                 575

Ala Arg Ser Val Val Ser Gln Pro Lys Val Leu Leu Leu Asp Glu Ala
                580                 585                 590

Thr Ser Ala Leu Asp Pro His Ala Glu Thr Ile Val Gln Lys Ala Leu
            595                 600                 605

Asp Lys Ala Ala Glu Gly Arg Thr Thr Ile Val Ile Ala His Lys Leu
        610                 615                 620

Ala Thr Ile Arg Lys Ala Asp Asn Ile Val Val Met Ser Lys Gly His
625                 630                 635                 640

Ile Val Glu Gln Gly Thr His Glu Ser Leu Ile Ala Lys Asp Gly Val
                645                 650                 655

Tyr Ala Gly Leu Val Lys Ile Gln Asn Leu Ala Val Asn Ala Ser Ala
                660                 665                 670

His Asp Asn Val Asn Glu Glu Gly Glu Gly Asp Val Ala Leu Leu
            675                 680                 685

Glu Val Thr Glu Thr Ala Val Thr Arg Tyr Pro Thr Ser Ile Arg Gly
```

-continued

```
            690                 695                 700
Arg Met Asn Ser Ile Lys Asp Arg Asp Asp Tyr Glu Asn His Lys His
705                 710                 715                 720

Met Asp Met Leu Ala Ala Leu Ala Tyr Leu Val Arg Glu Cys Pro Glu
            725                 730                 735

Leu Lys Trp Ala Tyr Leu Val Val Leu Leu Gly Cys Leu Gly Gly Cys
            740                 745                 750

Ala Met Tyr Pro Gly Gln Ala Ile Leu Met Ser Arg Val Val Glu Val
            755                 760                 765

Phe Thr Leu Ser Gly Asp Ala Met Leu Asp Lys Gly Asp Phe Tyr Ala
            770                 775                 780

Ser Met Leu Ile Val Leu Ala Ala Gly Cys Leu Ile Cys Tyr Leu Ala
785                 790                 795                 800

Val Gly Tyr Ala Thr Asn Thr Ile Ala Gln His Leu Ser His Trp Phe
            805                 810                 815

Arg Arg Leu Ile Leu His Asp Met Leu Arg Gln Asp Ile Gln Phe Phe
            820                 825                 830

Asp Arg Glu Glu Asn Thr Thr Gly Ala Leu Val Ser Arg Ile Asp Ser
            835                 840                 845

Tyr Pro His Ala Ile Leu Glu Leu Met Gly Tyr Asn Ile Ala Leu Val
            850                 855                 860

Val Ile Ala Val Leu Gln Val Val Thr Cys Gly Ile Leu Ala Ile Ala
865                 870                 875                 880

Phe Ser Trp Lys Leu Gly Leu Val Val Phe Gly Gly Ile Pro Pro
            885                 890                 895

Leu Val Gly Ala Gly Met Val Arg Ile Arg Val Asp Ser Arg Leu Asp
            900                 905                 910

Arg Gln Thr Ser Lys Lys Tyr Gly Thr Ser Ser Ile Ala Ser Glu
            915                 920                 925

Ala Val Asn Ala Ile Arg Thr Val Ser Ser Leu Ala Ile Glu Glu Thr
            930                 935                 940

Val Leu Arg Arg Tyr Thr Glu Glu Leu Asp His Ala Val Ser Ser Ser
945                 950                 955                 960

Val Lys Pro Met Ala Ala Thr Met Ile Cys Phe Gly Leu Thr Gln Cys
            965                 970                 975

Ile Glu Tyr Trp Phe Gln Ala Leu Gly Phe Trp Tyr Gly Cys Arg Leu
            980                 985                 990

Val Ser Leu Gly Glu Thr Ser Met Tyr Ser Phe Val Ala Phe Leu
            995                 1000                1005

Ser Val Phe Phe Ala Gly Gln Ala Ser Ala Gln Leu Phe Gln Trp Ser
            1010                1015                1020

Thr Ser Ile Thr Lys Gly Ile Asn Ala Thr Asn Tyr Ile Ala Trp Leu
1025                1030                1035                1040

His Gln Leu Gln Pro Thr Val Arg Glu Thr Pro Glu Asn His Asp Lys
            1045                1050                1055

Gly Pro Gly Ser Gly Ala Pro Ile Ala Met Asp Asn Val Arg Phe Ser
            1060                1065                1070

Tyr Pro Leu Arg Pro Asp Ala Pro Ile Leu Lys Gly Val Asn Leu Lys
            1075                1080                1085

Ile Asn Lys Gly Gln Phe Ile Ala Phe Val Gly Ser Ser Gly Cys Gly
            1090                1095                1100

Lys Ser Thr Met Ile Ala Met Leu Glu Arg Phe Tyr Asp Pro Thr Thr
1105                1110                1115                1120
```

```
Gly Ser Ile Thr Ile Asp Ala Ser Thr Leu Thr Asp Ile Asn Pro Ile
            1125                1130                1135

Ser Tyr Arg Asn Ile Val Ala Leu Val Gln Gln Glu Pro Thr Leu Phe
            1140                1145                1150

Gln Gly Thr Ile Arg Asp Asn Ile Ser Leu Gly Asp Ala Val Lys Ser
            1155                1160                1165

Val Ser Asp Glu Gln Ile Glu Ser Ala Leu Arg Ala Ala Asn Ala Trp
1170                1175                1180

Asp Phe Val Ser Ser Leu Pro Gln Gly Ile Tyr Thr Pro Ala Gly Ser
1185                1190                1195                1200

Gly Gly Ser Gln Leu Ser Gly Gly Gln Arg Gln Arg Ile Ala Ile Ala
            1205                1210                1215

Arg Ala Leu Ile Arg Asp Pro Lys Ile Leu Leu Leu Asp Glu Ala Thr
            1220                1225                1230

Ser Ala Leu Asp Thr Glu Ser Glu Lys Ile Val Gln Lys Ala Leu Glu
            1235                1240                1245

Gly Ala Ala Arg Asp Gly Asp Arg Leu Thr Val Ala Val Ala His Arg
            1250                1255                1260

Leu Ser Thr Ile Lys Asp Ala Asn Val Ile Cys Val Phe Phe Gly Gly
1265                1270                1275                1280

Lys Ile Ala Glu Met Gly Thr His Gln Glu Leu Ile Val Arg Gly Gly
            1285                1290                1295

Leu Tyr Arg Arg Met Cys Glu Ala Gln Ala Leu Asp
            1300                1305

(2) INFORMATION FOR SEQ ID NO:3:

(i) SEQUENCE CHARACTERISTICS:
        (A) LENGTH: 3924 base pairs
        (B) TYPE: nucleic acid
        (C) STRANDEDNESS: single
        (D) TOPOLOGY: linear (ii) MOLECULE TYPE: mRNA (iii) HYPOTHETICAL: NO (iv) ANTI-SENSE: NO (xi) SEQUENCE DESCRIPTION: SEQ ID NO:3:

AUGCGGAGGC UCGGACCCUC AGUUUACCGG CGUUCGGACG UGUCUACUUU AAAAAAAAAG      60

AAGCUCUCGU UGUCACCAUC GUCAUGCUCG ACCGCGGCUG UACCAGACUC CGUCUCAGGA     120

CGAGUCGACC ACCAGUGUAC CAUGCACGGA GGCGCCUCUG GUCGAGGAAG GGGAGGAAGC     180

AAGCUUUGGC GCAUACAAGG UGCCAAGCUG AUAUGCUCGC GCAAAAGAGG AUCUUUACAU     240

UCGCCGGCAG GACAGAACUU AUCCUUCAGG CCGUUGCUAU CCUUGCUGCA UGCGCCUCUG     300

GAGCAGGAAU UGCGCUUCAA AACCUCAUCU UCGGCCAGUU CGUCACCGUC AUCACCGAUU     360

UCACCAACGG AAUCUCAACG CCGGCAGACU UUCGUGACAA UGCCGCCGAG UUGGCGUAUC     420

CUCUACUUUG UAUACCUGGG CAUCGCGCGG CUCGUCCUCU CCUACACCUA CAACACCCUC     480

CUAACCUACG CGGCCUACCG CAUCGUCCGC AAUAUCCGAC ACGCCUAUCU CAAAGCGGCG     540

CUGAGCCAAG AAGUGGCAUA CUACGAUUUC GGUAGCGGGG GCUCCAUCGC CGCGCAGGCA     600

ACUUCGAACG GCAAACUGAU CCAGGCCGGC GCCUCGGAUA AGAUCGGUCU UCUCUUCCAG     660

GGCCUCGCAG CAUUCGUGAC GCUUUCAUUA UCGCGUUUGU GGUGCAAGUG GAAACUCACU     720

CUGAUCUGCA UCUGCAUCCC CGUAGCCACG AUCGGCACGA CGGGGGUGGU AGCUGCGGUC     780

GAGGCUGGGC ACGAGACGAG GAUCUUGCAG AUACAUGCGC AGGCGAAUUC GUUUGCCGAG     840
```

```
GGUAUUCUGG CGGGUGUGAA GGCUGUUCAU GCUUUUGGGA UGCGGGAUAG UCUGGUCAGG      900

AAGUUUGAUG AAUAUCUGGU GGAGGCGCAU AAGGUCGGUA AGAAGAUCUC GCCGCUGCUU      960

GGUCUUCUCU UCUCGGCGGA GUAUACGAUC AUCUACCUUG GAUAUGGGCU GGCGUUUUGG     1020

CAGGGGAUCC AUAUGUUCGG CAGGGGGAG AUUGGGACUG CUGGGGAUAU CUUUACGGUU     1080

UUGCUCUCUG UCGUCAUUGC GUCAAUCAAC CUGACUUUAC UGGCGCCGUA UUCAUUGAA      1140

UUUAGCAGGG CUGCUUCAGC GGCUGCGCAA CUGUUCCGAC UCAUAGAUCG AGAGUCUGAA     1200

AUCAACCCAU ACGGGAAGGA AGGCCUCGAG CCGGAACGGG UAUUAGGCGA CGUCGAGCUC     1260

GAGAAUGUUA CGUUCUCGUA UCCCACGAGG CCGGGGAUUA CCGUCCUCGA UAACUUCAGU     1320

CUCAAGGUCC CAGCGGGAAA GGUGACUGCC CUGGUAGGGC AAUCUGGAUC GGGGAAGAGC     1380

ACGAUCGUGG GAUUGCUCGA GCGGUGGUAU AACCCGACCU CUGGGGCGAU CAGACUCGAC     1440

GGGAACCUGA UCAGUGAGCU CAAUGUUGGC UGGCUGCGGA GGAAUGUGCG GCUCGUACAG     1500

CAGGAGCCGG UGCUCUUCCA GGGAAGCGUG UUCGAUAACA UCAGGUACGG CCUCGUCGGG     1560

ACGCCGUGGG AGAAUGCCUC UCGGGAAGAG CAGAUGGAAC GGGUGCAGGA GGCCGCGAAG     1620

UUGGCAUAUG CGCACGAAUU CAUCUCUGAG CUGACCGACG GAUACGAUAC GCUGAUCGGC     1680

GAACGGGGUG GUCUGCUUUC UGGAGGCCAG AAGCAGCGGG UUGCGAUUGC CGCAGCGUC      1740

GUUUCUCAAC CGAAGGUCCU UCUGCUGGAU GAAGCAACCA GUGCUCUUGA UCCGCAUGCA     1800

GAGACGAUUG UUCAGAAGGC UCUGGACAAA GCAGCUGAGG GGCGCACGAC GAUUGUCAUU     1860

GCUCACAAAC UUGCUACGAU CCGCAAGGCG GACAAUAUCG UUGUCAUGAG CAAGGGUCAC     1920

AUUGUCGAGC AAGGCACACA CGAGUCACUG AUAGCCAAGG ACGGCGUCUA UGCCGGUCUG     1980

GUCAAAAUCC AGAACCUGGC AGUGAAUGCU UCAGCACAUG ACAAUGUAAA UGAGGAGGGU     2040

GAAGGCGAAG AUGUCGCUCU CCUGGAGGUC ACCGAAACAG CAGUAACCCG CUACCCAACC     2100

UCCAUCCGCG GUCGAAUGAA CUCCAUAAAG GACCGCGACG AUUAUGAGAA CCACAAGCAC     2160

AUGGAUAUGC UGGCCGCCUU AGCUUAUCUC GUCCGCGAAU GUCCAGAACU GAAAUGGGCC     2220

UAUCUCGUCG UGCUACUGGG GUGUCUUGGU GGUUGCGCCA UGUACCCCGG CCAAGCUAUC     2280

UUGAUGUCUC GCGUUGUCGA GGUCUUCACG CUCUCGGGAG ACGCUAUGCU AGACAAAGGA     2340

GACUUCUAUG CCAGUAUGCU GAUCGUUCUC GCGGCCGGGU GUCUGAUCUG UUACUUAGCU     2400

GUCGGAUAUG CAACCAACAC UAUAGCCCAG CAUCUUAGUC AUUGGUUUCG ACGCCUCAUU     2460

CUGCACGACA UGCUGCGACA GGAUAUCCAG UUCUUUGACC GUGAAGAGAA CACUACCGGU     2520

GCGCUGGUAA GCCGUAUCGA UUCGUACCCG CAUGCAAUUC UCGAACUGAU GGGCUACAAC     2580

AUCGCCCUGG UCGUGAUUGC UGUCCUGCAG GUGGUAACCU GGGCAUCCU GGCCAUUGCA      2640

UUCUCCUGGA AACUAGGGCU GGUCGUUGUC UUUGGCGGUA UUCCACCCCU UGUCGGUGCU     2700

GGGAUGGUAC GAAUCCGCGU CGACUCCCGC CUCGAUCGCC AGACAUCGAA GAAAUAUGGC     2760

ACCAGCUCGU CCAUUGCCUC UGAAGCUGUA AACGCUAUCC GGACCGUUUC GUCCCUUGCA     2820

AUCGAAGAGA CGGUGCUACG UCGAUACACG GAGGAACUAG ACCACGCUGU UCGUCUUCG      2880

GUGAAACCCA UGGCUGCCAC GAUGAUUUGU UCGGGCUGA CGCAGUGCAU UGAGUACUGG      2940

UUUCAGGCGC UGGGAUUCUG GUAUGGGUGU CGUCUUGUGU CGCUGGGGGA GACUAGCAUG     3000

UAUAGUUUCU UUGUCGCAUU CCUCAGUGUG UUCUUGCGG GUCAGGCGUC AGCGCAGCUG      3060

UUCCAGUGGU CGACCAGUAU UACAAAGGGA AUCAAUGCGA CGAACUACAU CGCUUGGUUG     3120

CACCAGCUCC AACCAACAGU GCGCGAGACG CCGGAGAACC ACGAUAAAGG CCCUGGAUCU     3180

GGGGCGCCGA UUGCUAUGGA CAAUGUGCGC UUCUCGUACC CUCUACGGCC AGACGCCCCU     3240
```

```
AUCCUGAAAG GGGUGAAUCU GAAGAUAAAC AAAGGCCAAU UCAUCGCUUU CGUCGGCUCC    3300

UCCGGCUGCG GCAAAUCCAC CAUGAUUGCC AUGCUCGAGC GCUUCUACGA UCCAACAACA    3360

GGGAGCAUCA CAAUCGACGC UUCCACCCUC ACCGACAUAA ACCCCAUAUC CUACCGAAAU    3420

AUUGUGGCAC UGGUGCAGCA AGAGCCAACC CUUUUCCAAG GGACAAUACG GGACAACAUC    3480

UCGCUUGGCG AUGCAGUGAA GUCCGUGUCU GAUGAGCAGA UUGAGUCGGC CCUCCGCGCA    3540

GCUAAUGCCU GGGACUUUGU CUCCUCAUUG CCGCAGGGGA UCUACACGCC CGCUGGCUCA    3600

GGCGGGUCCC AACUCUCUGG GGGGCAGCGG CAACGCAUUG CCAUUGCCCG CGCGCUCAUC    3660

CGAGAUCCAA AGAUCUUACU CCUUGACGAG GCUACGAGUG CCCUGGAUAC AGAGAGUGAG    3720

AAGAUCGUGC AGAAGGCUCU CGAGGGGCG GCCAGGGACG GGGACCGGCU UACGGUUGCU     3780

GUUGCGCAUC GAUUAAGCAC GAUUAAGGAU GCUAAUGUUA UCUGUGUAUU CUUUGGAGGA    3840

AAGAUUGCGG AGAUGGGAAC GCAUCAAGAG UUAAUAGUUA GGGGGGGGCU GUAUAGACGG    3900

AUGUGUGAGG CGCAGGCCUU GGAC                                          3924
```

MULTIPLE DRUG RESISTANCE GENE ATRC OF ASPERGILLUS NIDULANS

TECHNICAL FIELD OF THE INVENTION

This invention relates to recombinant DNA technology. In particular, the invention concerns the cloning of nucleic acid encoding a multiple drug resistance protein of *Aspergillus nidulans*.

BACKGROUND OF THE INVENTION

Multiple drug resistance (MDR) mediated by the human mdr-1 gene product was initially recognized during the course of developing regimens for cancer chemotherapy (Fojo et al., 1987, *Journal of Clinical Oncology* 5:1922–1927). A multiple drug resistant cancer cell line exhibits resistance to high levels of a large variety of cytotoxic compounds. Frequently these cytotoxic compounds will have no common structural features nor will they interact with a common target within the cell. Resistance to these cytotoxic agents is mediated by an outward directed, ATP-dependent pump encoded by the mdr-1 gene. By this mechanism, toxic levels of a particular cytotoxic compound are not allowed to accumulate within the cell.

MDR-like genes have been identified in a number of divergent organisms including numerous bacterial species, the fruit fly *Drosophila melanogaster*, *Plasmodium falciparum*, the yeast *Saccharomyces cerevisiae*, *Caenorhabditis elegans*, *Leishmania donovanii*, marine sponges, the plant *Arabidopsis thaliana*, as well as *Homo sapiens*. Extensive searches have revealed several classes of compounds that are able to reverse the MDR phenotype of multiple drug resistant human cancer cell lines rendering them susceptible to the effects of cytotoxic compounds. These compounds, referred to herein as "MDR inhibitors", include for example, calcium channel blockers, antiarrhythmics, antihypertensives, antibiotics, antihistamines, immuno-suppressants, steroid hormones, modified steroids, lipophilic cations, diterpenes, detergents, antidepressants, and antipsychotics (Gottesman and Pastan, 1993, *Annual Review of Biochemistry* 62:385–427). Clinical application of human MDR inhibitors to cancer chemotherapy has become an area of intensive focus for research.

On another front, the discovery and development of antifungal compounds for specific fungal species has also met with some degree of success. Candida species represent the majority of fungal infections, and screens for new antifungal compounds have been designed to discover anti-Candida compounds. During development of antifungal agents, activity has generally been optimized based on activity against *Candida albicans*. As a consequence, these anti-Candida compounds frequently do not possess clinically significant activity against other fungal species such as *Aspergillus nidulans*. However, it is interesting to note that at higher concentrations some anti-Candida compounds are able to kill other fungal species such as *A. fumigatus* and *A. nidulans*. This type of observation suggests that the antifungal target(s) of these anti-Candida compounds is present in *A. fumigatus* and *A. nidulans* as well. Such results indicate that *A. nidulans* may possess a natural mechanism of resistance that permits them to survive in clinically relevant concentrations of antifungal compounds. Until the present invention, such a general mechanism of resistance to antifungal compounds in *A. nidulans* has remained undescribed.

SUMMARY OF THE INVENTION

The invention provides, inter alia, isolated nucleic acid molecules that comprise nucleic acid encoding a multiple drug resistance protein from *Aspergillus nidulans*, herein referred to as atrC, vectors encoding atrC, and host cells transformed with these vectors.

In another embodiment, the invention provides a method for determining the fungal MDR inhibition activity of a compound which comprises:

a) placing a culture of fungal cells, transformed with a vector capable of expressing atrC, in the presence of:
  (i) an antifungal agent to which said fungal cell is resistant, but to which said fungal cell is sensitive in its untransformed state;
  (ii) a compound suspected of possessing fungal MDR inhibition activity; and
b) determining the fungal MDR inhibition activity of said compound by measuring the ability of the antifungal agent to inhibit the growth of said fungal cell.

In still another embodiment the present invention relates to strains of *A. nidulans* in which the atrC gene is disrupted or otherwise mutated such that the atrC protein is not produced in said strains.

In yet another embodiment, the present invention relates to a method for identifying new antifungal compounds.

DETAILED DESCRIPTION OF THE INVENTION

The present invention provides isolated nucleic acid molecules that comprise a nucleic acid sequence encoding atrC. The cDNA (complementary deoxyribonucleic acid) sequence encoding atrC is provided in the Sequence Listing as SEQ ID NO: 1. The amino acid sequence of the protein encoded by atrC is provided in the Sequence Listing as SEQ ID NO: 2.

Those skilled in the art will recognize that the degenerate nature of the genetic code enables one to construct many different nucleic acid sequences that encode the amino acid sequence of SEQ ID NO: 2. The cDNA sequence depicted by SEQ ID NO: 1 is only one of many possible atrC-encoding sequences. Consequently, the constructions described below and in the accompanying examples for the preferred nucleic acid molecules, vectors, and transformants of the invention are illustrative and are not intended to limit the scope of the invention.

All nucleotide and amino acid abbreviations used in this disclosure are those accepted by the United States Patent and Trademark Office as set forth in 37 C.F.R. §1.822(b) (1994).

The term "vector" refers to any autonomously replicating or integrating agent, including but not limited to plasmids, cosmids, and viruses (including phage), comprising a nucleic acid molecule to which one or more additional nucleic acid molecules can be added. Included in the definition of "vector" is the term "expression vector". Vectors are used either to amplify and/or to express deoxyribonucleic acid (DNA), either genomic or cDNA, or RNA (ribonucleic acid) which encodes atrC, or to amplify DNA or RNA that hybridizes with DNA or RNA encoding atrC.

The term "expression vector" refers to vectors which comprise a transcriptional promoter (hereinafter "promoter") and other regulatory sequences positioned to drive expression of a DNA segment that encodes atrC. Expression vectors of the present invention are replicable DNA constructs in which a DNA sequence encoding atrC is operably linked to suitable control sequences capable of effecting the expression of atrC in a suitable host. Such control sequences include a promoter, an optional operator sequence to control transcription, a sequence encoding suitable mRNA ribosomal binding sites, and sequences which control termination of transcription and translation. DNA regions are operably linked when they are functionally related to each other. For example, a promoter is operably linked to a DNA coding sequence if it controls the transcription of the sequence, or a ribosome binding site is operably linked to a coding sequence if it is positioned so as to permit translation.

The term "MDR inhibition activity" refers to the ability of a compound to inhibit the MDR activity of a host cell, thereby increasing the antifungal activity of an antifungal compound against said host cell.

In the present invention, atrC may be synthesized by host cells transformed with vectors that provide for the expression of DNA encoding atrC. The DNA encoding atrC may be the natural sequence or a synthetic sequence or a combination of both ("semi-synthetic sequence"). The in vitro or in vivo transcription and translation of these sequences results in the production of atrC. Synthetic and semi-synthetic sequences encoding atrC may be constructed by techniques well known in the art. See Brown et al. (1979) *Methods in Enzymology*, Academic Press, N.Y., 68:109–151. atrC-encoding DNA, or portions thereof, may be generated using a conventional DNA synthesizing apparatus such as the Applied Biosystems Model 380A, 380B, 394 or 3948 DNA synthesizers (commercially available from Applied Biosystems, Inc., 850 Lincoln Center Drive, Foster City, Calif. 94404).

Owing to the natural degeneracy of the genetic code, the skilled artisan will recognize that a sizable yet definite number of nucleic acid sequences may be constructed which encode atrC. All such nucleic acid sequences are provided by the present invention. These sequences can be prepared by a variety of methods and, therefore, the invention is not limited to any particular preparation means. The nucleic acid sequences of the invention can be produced by a number of procedures, including DNA synthesis, cDNA cloning, genomic cloning, polymerase chain reaction (PCR) technology, or a combination of these approaches. These and other techniques are described by Maniatis, et al., *Molecular Cloning: A Laboratory Manual*, Cold Spring Harbor Press, Cold Spring Harbor Laboratory, Cold Spring Harbor, N.Y. (1989), or *Current Protocols in Molecular Biology* (F. M. Ausubel et al., 1989 and supplements). The contents of both of these references are incorporated herein by reference.

In another aspect, this invention provides the genomic DNA encoding atrC, which may be obtained by synthesizing the desired portion of SEQ ID No. 1 or by following the procedure carried out by Applicants. This procedure involved construction of a cosmid genomic DNA library from *Aspergillus nidulans* strain OC-1, a mutant derived from A42355. This library was screened for genes related to MDRs using a homologous probe generated by PCR. Degenerate PCR primers directed towards amplification of DNA sequences encoding highly conserved regions found in the ATP-binding domain of several MDR genes were synthesized. PCR using these primers and *Aspergillus nidulans* genomic DNA as template produced an approximately 400 base pair DNA fragment. The DNA sequence of this fragment was highly homologous to the ATP-binding region of several MDRs as predicted. This fragment was used as a hybridization probe to identify cosmid clones containing the entire atrC gene. A subclone from one such cosmid containing the entire atrC gene was sequenced to ascertain the entire sequence of atrC.

To effect the translation of atrC-encoding mRNA, one inserts the natural, synthetic, or semi-synthetic atrC-encoding DNA sequence into any of a large number of appropriate expression vectors through the use of appropriate restriction endonucleases and DNA ligases. Synthetic and semi-synthetic atrC-encoding DNA sequences can be designed, and natural atrC-encoding nucleic acid can be modified, to possess restriction endonuclease cleavage sites to facilitate isolation from and integration into these vectors. Particular restriction endonucleases employed will be dictated by the restriction endonuclease cleavage pattern of the expression vector utilized. Restriction enzyme sites are chosen so as to properly orient the atrC-encoding DNA with the control sequences to achieve proper in-frame transcription and translation of the atrC molecule. The atrC-encoding DNA must be positioned so as to be in proper reading frame with the promoter and ribosome binding site of the expression vector, both of which are functional in the host cell in which atrC is to be expressed.

Expression of atrC in fungal cells, such as *Saccharomyces cerevisiae* is preferred. Suitable promoter sequences for use with yeast hosts include the promoters for 3-phosphoglycerate kinase (found on plasmid pAP12BD (ATCC 53231) and described in U.S. Pat. No. 4,935,350, Jun. 19, 1990) or other glycolytic enzymes such as enolase (found on plasmid pAC1 (ATCC 39532)), glyceraldehyde-3-phosphate dehydrogenase (derived from plasmid pHc-GAPC1 (ATCC 57090, 57091)), hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Inducible yeast promoters have the additional advantage of transcription controlled by growth conditions. Such promoters include the promoter regions for alcohol dehydrogenase 2, isocytochrome C, acid phosphotase, degradative enzymes associated with nitrogen metabolism, metallothionein (contained on plasmid vector pCL28XhoLHBPV (ATCC 39475), U.S. Pat. No. 4,840, 896), glyceraldehyde 3-phosphate dehydrogenase, and enzymes responsible for maltose and galactose utilization (GAL1 found on plasmid pRY121 (ATCC 37658) and on plasmid pPST5, described below). Suitable vectors and promoters for use in yeast expression are further described by R. Hitzeman et al., in European Patent Publication No. 73,657A. Yeast enhancers such as the UAS Gal enhancer from *Saccharomyces cerevisiae* (found in conjunction with the CYC1 promoter on plasmid YEpsec—hI1beta, ATCC 67024), also are advantageously used with yeast promoters.

A variety of expression vectors useful in the present invention are well known in the art. For expression in Saccharomyces, the plasmid YRp7, for example, (ATCC-40053, Stinchcomb et al., 1979, *Nature* 282:39; Kingsman et al., 1979, *Gene* 7:141; Tschemper et al., 1980, *Gene* 10:157) is commonly used. This plasmid contains the trp gene which provides a selection marker for a mutant strain of yeast lacking the ability to grow in tryptophan, for example ATCC 44076 or PEP4-1 (Jones, 1977, *Genetics* 85:12).

Expression vectors useful in the expression of atrC can be constructed by a number of methods. For example, the cDNA sequence encoding atrC can be synthesized using DNA synthesis techniques such as those described above. Such synthetic DNA can be synthesized to contain cohesive ends that allow facile cloning into an appropriately digested expression vector. For example, the cDNA encoding atrC can be synthesized to contain NotI cohesive ends. Such a synthetic DNA fragment can be ligated into a NotI-digested expression vector such as pYES-2 (Invitrogen Corp., San Diego Calif. 92121).

An expression vector can also be constructed in the following manner. Logarithmic phase *Aspergillus nidulans* cells are disrupted by grinding under liquid nitrogen according to the procedure of Minuth et al., 1982 (*Current Genetics* 5:227–231). *Aspergillus nidulans* mRNA is preferably isolated from the disrupted cells using the QuickPrep® mRNA Purification Kit (Pharmacia Biotech) according to the instructions of the manufacturer. cDNA is produced from the isolated mRNA using the TimeSaver® cDNA Synthesis Kit (Pharmacia Biotech) using oligo (dT) according to the procedure described by the manufacturer. In this process an EcoRI/NotI adapter (Stratagene, Inc.) is ligated to each end of the double stranded cDNA. The adapter modified cDNA is ligated into the vector Lambda Zap$^R$II® using the Predigested Lambda Zap$^R$II®/EcoRI/CIAP Cloning Kit (Stratagene, Inc.) according to the instructions of the manufacturer to create a cDNA library.

The library is screened for full-length cDNA encoding atrC using a $^{32}$P-radiolabeled fragment of the atrC gene. In this manner, a full-length cDNA clone is recovered from the *Aspergillus nidulans* cDNA library. A full-length cDNA clone recovered from the library is removed from the Lambda Zap$^R$II® vector by digestion with the restriction endonuclease NotI which produces a DNA fragment encoding atrC. This plasmid further comprises the ColE1 origin of replication which allows replication in *E. coli*, and the ampicillin resistance gene for selection of *E. coli* transformants. The expression plasmid further comprises the yeast 2μ origin of replication (2μ ori), allowing replication in yeast host cells, the yeast URA3 gene for selection of *S. cerevisiae* cells transformed with the plasmid grown in a medium lacking uracil, and the origin of replication from the f1 filamentous phage.

In a preferred embodiment of the invention *Saccharomyces cerevisiae* INVSc1 or INVSc2 cells (Invitrogen Corp., Sorrento Valley Blvd., San Diego Calif. 92121) are employed as host cells, but numerous other cell lines are available for this use. The transformed host cells are plated on an appropriate medium under selective pressure (minimal medium lacking uracil). The cultures are then incubated for a time and temperature appropriate to the host cell line employed.

The techniques involved in the transformation of yeast cells such as *Saccharomyces cerevisiae* cells are well known in the art and may be found in such general references as Ausubel et al., *Current Protocols in Molecular Biology* (1989), John Wiley & Sons, New York, N.Y. and supplements. The precise conditions under which the transformed yeast cells are cultured is dependent upon the nature of the yeast host cell line and the vectors employed.

Nucleic acid, either RNA or DNA, which encodes atrC, or a portion thereof, is also useful in producing nucleic acid molecules useful in diagnostic assays for the detection of atrC mRNA, atrC cDNA, or atrC genomic DNA. Further, nucleic acid, either RNA or DNA, which does not encode atrC, but which nonetheless is capable of hybridizing with atrC-encoding DNA or RNA is also useful in such diagnostic assays. These nucleic acid molecules may be covalently labeled by known methods with a detectable moiety such as a fluorescent group, a radioactive atom or a chemiluminescent group. The labeled nucleic acid is then used in conventional hybridization assays, such as Southern or Northern hybridization assays, or polymerase chain reaction assays (PCR), to identify hybridizing DNA, cDNA, or RNA molecules. PCR assays may also be performed using unlabeled nucleic acid molecules. Such assays may be employed to identify atrC vectors and transformants and in in vitro diagnosis to detect atrC-like mRNA, cDNA, or genomic DNA from other organisms.

U.S. patent application Ser. No. 08/111680, the entire contents of which are hereby incorporated herein by reference, describes the use of combination therapy involving an antifungal agent possessing a proven spectrum of activity, with a fungal MDR inhibitor to treat fungal infections. This combination therapy approach enables an extension of the spectrum of antifungal activity for a given antifungal compound which previously had only demonstrated limited clinically relevant antifungal activity. Similarly, compounds with demonstrated antifungal activity can also be potentiated by a fungal MDR inhibitor such that the antifungal activity of these compounds is extended to previously resistant species. To identify compounds useful in such combination therapy the present invention provides an assay method for identifying compounds with *Aspergillus nidulans* MDR inhibition activity. Host cells that express atrC provide an excellent means for the identification of compounds useful as inhibitors of *Aspergillus nidulans* MDR activity. Generally, the assay utilizes a culture of a yeast cell transformed with a vector which provides expression of atrC. The expression of atrC by the host cell enables the host cell to grow in the presence of an antifungal compound to which the yeast cell is sensitive to in the untransformed state. Thus, the transformed yeast cell culture is grown in the presence of i) an antifungal agent to which the untransformed yeast cell is sensitive, but to which the transformed host cell is resistant, and ii) a compound that is suspected of being an MDR inhibitor. The effect of the suspected MDR inhibitor is measured by testing for the ability of the antifungal compound to inhibit the growth of the transformed yeast cell. Such inhibition will occur if the suspected *Aspergillus nidulans* MDR inhibitor blocks the ability of atrC to prevent the antifungal compound from acting on the yeast cell. An illustrative example of such an assay is provided in Example 3.

In order to illustrate more fully the operation of this invention, the following examples are provided, but are not to be construed as a limitation on the scope of the invention.

EXAMPLE 1

Source of the atrC-Encoding Genomic DNA and cDNA of *Aspergillus nidulans*

Complementary DNA encoding atrC (sequence presented in SEQ ID NO: 1) may be from a natural sequence, a synthetic source or a combination of both ("semi-synthetic sequence"). The in vitro or in vivo transcription and translation of these sequences results in the production of atrC. Synthetic and semi-synthetic sequences encoding atrC may be constructed by techniques well known in the art. See Brown et al. (1979) *Methods in Enzymology*, Academic Press, N.Y., 68:109–151. atrC-encoding DNA, or portions thereof, may be generated using a conventional DNA synthesizing apparatus such as the Applied Biosystems Model 380A, 380B, 384 or 3848 DNA synthesizers (commercially available from Applied Biosystems, Inc., 850 Lincoln Center Drive, Foster City, Calif., 94404). The polymerase chain reaction is especially useful in generating these DNA sequences. PCR primers are constructed which include the translational start (ATG) and translational stop codon (TAG) of atrC. Restriction enzyme sites may be included on these PCR primers outside of the atrC coding region to facilitate rapid cloning into expression vectors. *Aspergillus nidulans* genomic DNA is used as the PCR template for synthesis of atrC including introns which is useful for expression studies in closely related fungi. In contrast, cDNA is used as the PCR template for synthesis of atrC devoid of introns which is useful for expression in foreign hosts such as *Saccharomyces cerevisiae* or bacterial hosts such as *Escherichia coli*.

EXAMPLE 2

Expression of the atrC Protein

*Saccharomyces cerevisiae* INVSc1 cells (Invitrogen Corp., San Diego Calif. 92191) are transformed with the plasmid containing atrC by the technique described by J. D. Beggs, 1988, *Nature* 275:104–109). The transformed yeast cells are grown in a broth medium containing YNB/CSM-Ura/raf (YNB/CSM-Ura [Yeast Nitrogen Base (Difco Laboratories, Detroit, Mich.) supplemented with CSM-URA (Bio 101, Inc.)] supplemented with 4% raffinose) at 28° C. in a shaker incubator until the culture is saturated. To induce expression of atrC, a portion of the culture is used to inoculate a flask containing YNB/CSM-Ura medium supplemented with 2% galactose (YNB/CSM-Ura/gal) rather than raffinose as the sole carbon source. The inoculated flask is incubated at 28° C. for about 16 hours.

EXAMPLE 3

Antifungal Potentiator Assay

Approximately $1 \times 10^6$ cells of a *Saccharomyces cerevisiae* INVSc1 culture expressing atrC are delivered to each of several agar plates containing YNB/CSM-Ura/gal. The agar surface is allowed to dry in a biohazard hood.

An antifungal compound that the untransformed yeast cell is typically sensitive to is dissolved in an appropriate solvent at a concentration that is biologically effective. Twenty μl of the solution is delivered to an antibiotic susceptibility test disc (Difco Laboratories, Detroit, Mich.). After addition of the antifungal solution the disc is allowed to air dry in a biohazard hood. When dry, the disc is placed on the surface of the petri plates containing the transformed *Saccharomyces cerevisiae* INVSc1 cells.

Compounds to be tested for the ability to inhibit atrC are dissolved in dimethylsulfoxide (DMSO). The amount of compound added to the DMSO depends on the solubility of the individual compound to be tested. Twenty ml of the suspensions containing a compound to be tested are delivered to an antibiotic susceptibility test disc (Difco Laboratories, Detroit, Mich.). The disc is then placed on the surface of the dried petri plates containing the transformed *Saccharomyces cerevisiae* INVSc1 cells approximately 2 cm from the antifungal-containing disc. Petri plates containing the two discs are incubated at 28° C. for about 16–48 hours.

Following this incubation period, the petri plates are examined for zones of growth inhibition around the discs. A zone of growth inhibition near the antifungal disc on the test plate indicates that the compound being tested for MDR inhibition activity blocks the activity of atrC and allows the antifungal compound to inhibit the growth of the yeast host cell. Such compounds are said to possess MDR inhibition activity. Little or no zone of growth inhibition indicates that the test compound does not block MDR activity and, thus, atrC is allowed to act upon the antifungal compound to prevent its activity upon the host cell.

EXAMPLE 4

Screen for Novel Antifungal Compounds

A plasmid molecule is constructed which contains DNA sequence information required for replication and genetic transformation in *E. coli* (e.g. ampicillin resistance). The plasmid also comprises DNA sequences encoding a marker for selection in fungal cells (e.g. hygromycin B phosphotransferase, phleomycin resistance, G418 resistance) under the control of an *A. nidulans* promoter. Additionally, the plasmid contains an internal portion of the atrC gene (e.g. about 3000 base pairs which lack 500 base pairs at the N-terminal end, and about 500 base pairs at the C-terminal end of the coding region specified by SEQ ID NO:1). The atrC gene fragment enables a single crossover gene disruption when transformed or otherwise introduced into *A. nidulans*.

Alternatively, a 5 kilobase pair to 6 kilobase pair region of *A. nidulans* genomic DNA containing the atrC gene is subcloned into the aforementioned plasmid. Then, a central portion of the atrC gene is removed and replaced with a selectable marker, such as hyromycin B phosphotransferase, for a double crossover gene replacement.

Gene disruption and gene replacement procedures for *A. nidulans* are well known in the art (See e.g. May et al, *J. Cell Biol.* 101, 712, 1985; Jones and Sealy-Lewis, *Curr. Genet.* 17, 81, 1990). Transformants are recovered on an appropriate selection medium, for example, hygromycin (if hygromycin B gene is used in the construction of disruption cassette). Gene replacement, or gene disruption, is verified by any suitable method, for example, by Southern blot hybridization.

Gene disruption or gene replacement strains are rendered hypersensitive to antifungal compounds, and are useful in screens for new antifungal compounds in whole cell growth inhibition studies.

---

We claim:

1. A DNA compound that comprises an isolated DNA sequence encoding SEQ ID NO: 2.

2. The DNA compound of claim 1 which comprises the isolated DNA sequence which is SEQ ID NO: 1.

3. A vector comprising an isolated DNA sequence of claim 1.

4. A vector comprising an isolated DNA sequence of claim 2.

5. A method for constructing a transformed host cell capable of expressing SEQ ID NO: 2, said method comprising transforming a host cell with a recombinant DNA vector that comprises an isolated DNA sequence of claim 1.

6. A method for expressing SEQ ID NO: 2 in a transformed host cell said method comprising culturing said transformed host cell of claim 5 under conditions suitable for gene expression.

7. An isolated DNA molecule of claim 1 or a portion thereof, which is labeled with a detectable moiety.

8. A host cell containing the vector of claim 3.

9. A host cell containing the vector of claim 4.

* * * * *